(12) United States Patent
Colaco et al.

(10) Patent No.: US 8,597,670 B2
(45) Date of Patent: Dec. 3, 2013

(54) WASH RESISTANT COMPOSITIONS CONTAINING AMINOSILICONE

(75) Inventors: Allwyn Colaco, Morristown, NJ (US); Xiaolan Wei, Suffern, NY (US); Bing C. Mei, Mahwah, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 13/313,463

(22) Filed: Dec. 7, 2011

(65) Prior Publication Data

US 2013/0149358 A1 Jun. 13, 2013

(51) Int. Cl.
*A61K 8/02* (2006.01)
*A61Q 5/02* (2006.01)

(52) U.S. Cl.
USPC ........................ 424/401; 424/70.122

(58) Field of Classification Search
USPC ........................... 424/401, 70.122
See application file for complete search history.

(56) References Cited

U.S. PATENT DOCUMENTS

| 6,328,950 | B1 | 12/2001 | Franzke et al. |
| 6,485,556 | B1 * | 11/2002 | DeLuca, Jr. ............ 106/415 |
| 7,699,897 | B2 | 4/2010 | Nguyen et al. |
| 2005/0214236 | A1 | 9/2005 | Peng et al. |
| 2007/0286837 | A1 * | 12/2007 | Torgerson et al. ....... 424/70.122 |

FOREIGN PATENT DOCUMENTS

| EP | 1312344 A2 | 5/2003 |
| GB | 2149806 A | 6/1985 |
| JP | 11-139820 A | 5/1999 |
| JP | 11-139946 | 5/1999 |
| JP | 2003095898 A2 | 4/2003 |

* cited by examiner

*Primary Examiner* — Brian-Yong Kwon
*Assistant Examiner* — Jennifer A Berrios
(74) *Attorney, Agent, or Firm* — David M. Joyal; Joan M. McGillycuddy; Brian C. Remy

(57) ABSTRACT

Compositions and methods are disclosed for imparting a long-wearing color to keratin fibers, including hair. More specifically, the invention relates to cosmetic compositions and methods for improving retention of particulate materials, such as pigments, on hair to artificially color the hair and/or to impart other aesthetic benefits to the hair. The compositions comprise at least one aminosilicone polymer having at least one diamino functional group, and a functional group equivalent weight (FGEW) from about 1,000 to about 2,000 g/mol and a non-spherical particulate material, preferably a pigment or a lake.

6 Claims, 4 Drawing Sheets

WASH RESISTANT COMPOSITIONS CONTAINING AMINOSILICONE

FIELD OF INVENTION

The present invention relates generally to durable and/or long-wearing cosmetic compositions. More specifically, the invention relates to cosmetic compositions for improving retention of particulate materials, such as pigments, on a keratinous substrate, such as hair, lips or skin, to artificially color the substrate and/or to impart other aesthetic benefits to the substrate.

BACKGROUND OF THE INVENTION

Consumers have utilized a number of cosmetic and personal care compositions to enhance and/or modify the appearance of keratin fibers, such as the hair. One popular modification is imparting an artificial color on the hair using a chemical dye. For example, the hair may be treated using a direct dye or an oxidative dye, which is also known as a "permanent" hair dye, to obtain a desired color. However, oxidative dyes can be harsh and damaging to the hair fibers.

Although imparting color to a keratinous substrate may be achieved by adhering color pigments to the hair, coloring compositions containing pigments are not resistant to transfer or removal, such as washing and/or shampooing of the hair. Typically, the compositions cannot retain pigment hair color beyond one shampooing or washing. In addition, pigments often lack compatibility with other cosmetic ingredients and tend to deposit competitively on hair substrates, causing other hair benefit agents to fail to deposit and bond with the substrates. Moreover, pigments are difficult to use in cosmetic applications that require detergents, conditioning agents, thickeners, silicones, solvents, inorganic and organic salts, humectants and other typical cosmetic ingredients. Furthermore, due to their insoluble nature, pigment-containing formulations are generally difficult to stabilize. Therefore, formulations containing pigments may lack several desirable consumer benefits.

Therefore, there is a need in the art for enhanced color retention and/or reduced color fading of hair artificially colored with compositions having pigments. It is therefore an object of the invention to provide compositions and methods for imparting enhanced color retention and reduced color fading to artificially colored hair.

SUMMARY OF THE INVENTION

In accordance with the foregoing objectives and others, the present invention provides methods and compositions for imparting a long-wearing color or aesthetic benefit as compared to an otherwise identical composition in the absence of said aminosilicone polymer.

In one aspect of the invention, a method is provided for imparting a long-wearing color or aesthetic benefit to keratin fibers, such as hair. The method comprises applying to the keratin fibers a composition having (a) at least one aminosilicone polymer having at least one diamino functional group and a functional group equivalent weight (FGEW) from about 1,000 to about 2,000 g/mol, and (b) a non-spherical particulate material. The presence of the aminosilicone polymer improves retention of said particulate material on the keratin fibers over time as compared to an otherwise identical composition in the absence of said aminosilicone. Preferably, the diamino functional group is a diamine-substituted alkyl group of the form $-(CH_2)_{1-6}-NR^N-(CH_2)_{1-6}-NR^N_2$, where $R^N$ is independently selected at each occurrence from hydrogen or lower alkyl. More preferably, the diamino functional group is an aminoethylaminopropyl group. In addition, the aminosilicone polymer may have a viscosity from about 500 to about 5,000 cP at 25° C.

In some embodiments, the aminosilicone polymer may be branched. In another embodiment, the aminosilicone polymer may have the structure:

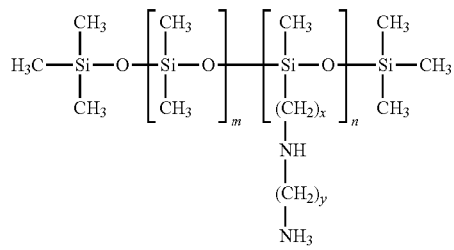

where
x is an integer from 1 to 6,
y is an integer from 1 to 6, and
m and n are independently each an integer from 1 to 5,000 and are selected to provide the aminosilicone polymer with an FGEW from about 1,000 to about 2,000 g/mol and/or to provide an overall molecular weight of the polymer such that the viscosity is from about 500 to about 5,000 cP at 25° C. Preferably, x is 3 and y is 2.

In another aspect of the invention, the non-spherical particulate material may preferably be a pigment or lake, preferably, an iron oxide. In particular, the non-spherical particulate material may have a plate-like or elongated shape.

In yet another aspect of the invention, a method is provided for imparting a long-wearing color or aesthetic benefit to keratin fibers comprising applying to the keratin fibers any of the inventive compositions. The compositions may be applied to the keratin fibers prior to shampooing or washing.

In yet another aspect of the invention, a method is provided for imparting a long-wearing color or aesthetic benefit to keratin fibers comprising applying to the keratin fibers the aminosilicone polymer of the invention followed by an application of a composition containing the particulate material of the invention. Hence in addition to a one step formula, a two step process is feasible in which the aminosilicone polymer and particulate materials are formulated separately. An example includes a shampoo containing aminosilicone and a conditioner containing the particulate material.

These and other aspects of the present invention will become apparent to those skilled in the art after a reading of the following detailed description of the invention, including the illustrative embodiments and examples.

DETAILED DESCRIPTION

Figure 1:
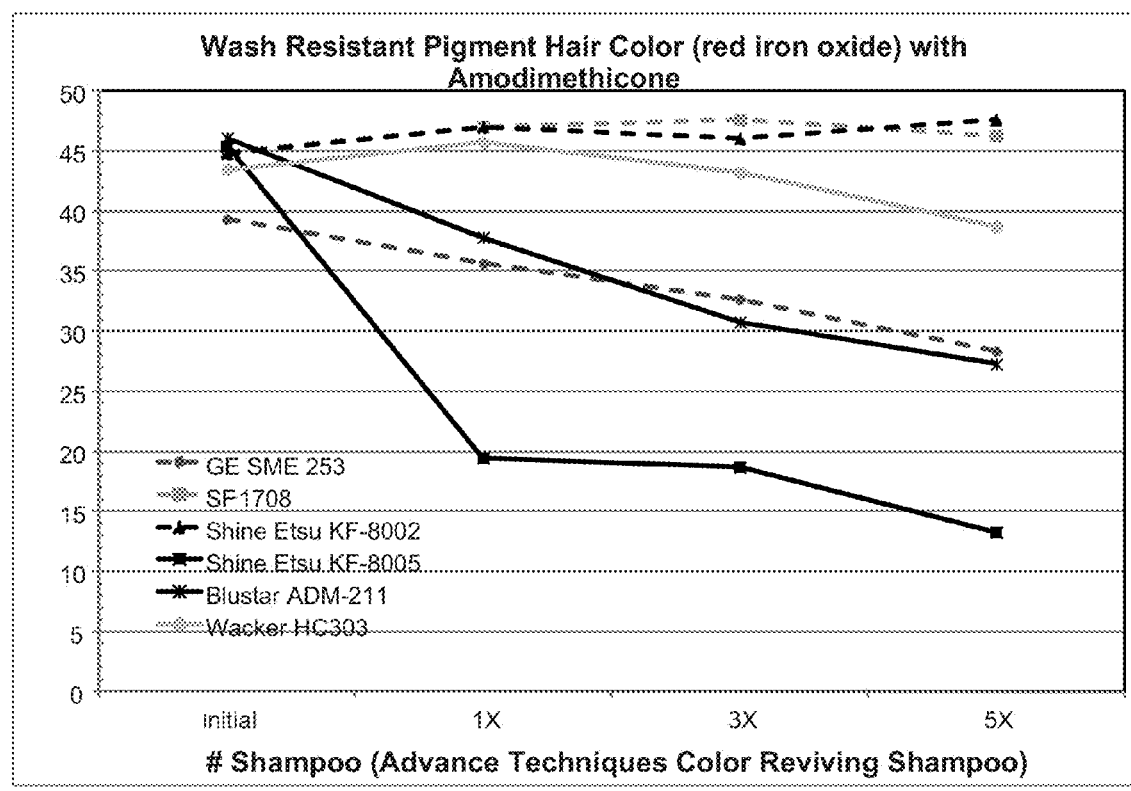
FIG. 1 shows results of a comparative color retention test for Samples 1 through 6 after five shampoo washes.

In the following description of the invention, it is to be understood that the terms used herein have their ordinary and accustomed meanings in the art, unless otherwise specified. All weights percentages referred to herein are given in terms of "% by weight" of the total composition, unless otherwise indicated.

Unless otherwise provided, the term "alkyl" is intended to embrace straight-chained, branched, or cyclic hydrocarbons, particularly those having from one to 20 carbon atoms, and more particularly $C_{1-12}$ hydrocarbons.

The compositions of the present invention can include, comprise, consist essentially of, or consist of the components of the present invention as well as other ingredients described herein. As used herein, "consisting essentially of" means that the composition or component may include additional ingredients, but only if the additional ingredients do not materially alter the basic and novel characteristics of the claimed compositions or methods.

As used herein, the term "keratin fiber" includes hair of the scalp, eyelashes, eyebrows, facial hair, and body hair such as hair of the arms, legs, etc. Keratin fibers are not limited to humans and also include any keratin fibers from a mammal, such as, for example, pet hair and mammalian fur.

As used herein, the term "functional group equivalent weight," or "FGEW," means the ratio of number-average molecular weight (NAVG MW) to the number of functional groups in the polymer.

The present invention is founded, in part, on the discovery that the addition of certain aminosilicones having at least one diamino-functional group having a specific range of functional group equivalent weights (FGEWs), where a low value reflects a high number of amino groups in the aminosilicone polymer, to a hair care composition improves retention of particulate materials, such as pigments, onto the hair. The composition of the present invention have been found to retain particulate materials onto keratin fibers, preferably hair, eyelashes, eyebrows, and beards, for a longer period of time as compared to an otherwise identical composition in the absence of the aminosilicone. Preferably, the inventive compositions may include a particulate coloring agent (e.g., pigments, including but not limited to, iron oxides) and impart a wash-resistant color for a longer period of time, particularly after repeated shampooing, as compared to an otherwise identical composition in the absence of the aminosilicone polymer. The compositions of the invention may also provide resistance to color transfer from hair to clothing.

Moreover, the compositions of the present invention may impart wash-resistant aesthetic benefits to the hair, particularly after repeated shampooing, such as conditioning, softness, manageability, and/or reduced fly-away hair, without a materially adverse effect on other aesthetic properties (e.g., appearance, feel, volume, shine, etc.) of the hair.

A first component of the hair care compositions of the present invention comprises at least one aminosilicone polymer having at least one diamino functional group (e.g., an aminoethylaminopropyl group). Generally, an aminosilicone will have a siloxane backbone and will be formed from the polymerization of (i) monomers of the form —O—Si—$(R)_2$—O—, where R is independently selected at each occurrence from lower alkyl groups, but is typically a methyl group at each occurrence, and (ii) monomers of the form —O—Si—(R(R*)—O—, where R is a lower alkyl group, typically a methyl, ethyl or propyl, especially a methyl, group, and R* is a diamine-substituted alkyl group of the form —$(CH_2)_{1-6}$—$NR^N$—$(CH_2)_{1-6}NR^N_2$, preferably —$(CH_2)_{2-4}$—$NR^N$—$(CH_2)_{2-4}$—$NR^N_2$, more preferably —$(CH_2)_3$—$NR^N$—$(CH_2)_2$—$NR^N_2$, where $R^N$ is independently selected at each occurrence from hydrogen or lower alkyl, typically a methyl, ethyl or propyl group, and most typically hydrogen. In specific embodiments, the R* is either a group —$(CH_2)_{1-6}$—NH—$(CH_2)_{1-6}$—$N_2$, typically a group —$(CH_2)_{2-4}$—NH—$(CH_2)_{1-3}$—$NH_2$, or more typically a group —$(CH_2)_3$—NH—$(CH_2)_2$ $NH_2$. The aminosilicone may have a linear or branched chemical structure. The ratio of siloxane monomer unit (i) amino-functionalized siloxane monomer unit (ii) in the polymer will be selected such that the functional group equivalent weight (FGEW) is from about 1,000 to about 2,000 g/mol, and the overall molecular weight of the polymer is such that the polymer viscosity is from about 500 to about 5,000 cP at 25° C.

Preferably, the FGEW of the aminosilicone polymer is from about 1,100 to about 1,900 g/mol. Embodiments according to the invention include wherein the aminosilicone polymer has an FGEW of 1,200, 1,250, 1,300, 1,400, 1,500, 1,600, 11,700 or 1,800 g/mol. More preferably, the FGEW of the aminosilicone polymer is from about 1,250 to about 1,800 g/mol.

Preferably, the viscosity of the aminosilicone is from about 1,000 to about 3,000 cP at 25° C. More preferably, the viscosity of the aminosilicone is from about 1,250 to about 2,500 cP at 25° C.

Preferably, the aminosilicone polymer will have the structure of Formula I:

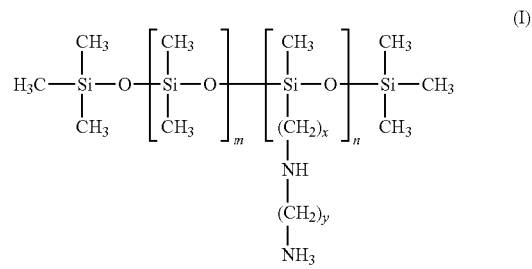

(I)

where x is an integer from 1 to 6, preferably from 2 to 5, more preferably from 2 to 4, and most preferably 3;

y is an integer from 1 to 6, preferably from 1 to 3, and more preferably 2; and m and n are independently each an integer from 1 to 5,000 and are selected to provide the aminosilicone polymer with an FGEW from about 1,000 to about 2,000 g/mol and/or to provide an overall molecular weight of the polymer such that the viscosity of the polymer is from about 500 to about 5,000 cP at 25° C.

One particularly preferred aminosilicone is available from Momentive Specialty Chemicals Inc. under the trade name SF1708. The SF1708 material is an aminopropylaminoethylpolysiloxane (CAS Reg. No. 71750-79-3), which has a FGEW of 1,250 g/mol, a molecular weight from 25,000 to 30,00 Daltons, and a viscosity of 1250-2500 cP at 25° C.

Other suitable aminosilicone polymers include the materials sold under the trade names KF-861, KF-880, KF-867, KF-8002 and KF-8004 available from Shin-Etsu Chemical Co., Ltd. The KF-861 material has a FGEW of 1,600 g/mol, a viscosity of 3,500 $mm^2/s$, a specific gravity of 0.98, and a refractive index of 1,408, all at 25° C. The KF-880 material has a FGEW of 1,800 g/mol, a viscosity of 650 $mm^2/s$, a specific gravity of 0.98, and a refractive index of 1,407, all at 25° C. The KF-867 material has a FGEW of 1,700 Owl, a viscosity of 1300 mm²/s, a specific gravity of 0.98, and a refractive index of 1,407, all at 25° C. The KF-8002 material has a FGEW of 1,700 g/mol, a viscosity of 1,100 mm²/s (25° C.), a specific gravity of 0.98 (25° C.), and a refractive index of 1,408 (25° C.). The KF-8004 material has a FGEW of 1,500 g/mol, a viscosity of 800 mm²/s (25° C.), a specific gravity of 0.98 (25° C.), and a refractive index of 1,408 (25° C.).

The aminosilicone polymer is typically present from about 0.01% to about 25% by weight of the total composition. More typically, the aminosilicone polymer will comprise from about 1% to about 15% by weight of the composition. Preferably, the aminosilicone polymer will comprise from about 5% to about 10% by weight of the composition, including embodiments wherein the aminosilicone polymer is present at about 6%, 7%, 8%, or 9% by weight of the composition.

A second component of the hair care compositions of the invention comprises a particulate material imparting a cosmetic benefit to the hair. The particulate material may be any particulate material suitable for use in a cosmetic composition. Advantageously, the particulate material may be one which provides color or other cosmetic functionality to the compositions, including for example, ultraviolet (UV) light absorption or scattering, in the case of, for example, titanium dioxide and zinc oxide particulates, or provide aesthetic characteristics, such as color (e.g., pigments), pearlesence (e.g., mica), or the like. Preferably, the particulate material includes pearlescents and coloring agents, such as pigments and/or lakes which are described in the *Cosmetic Ingredient Handbook, First Edition*, J. M. Nikitakis, et al., Cosmetic, Toiletry, and Fragrance Association, Washington, D.C., 1988, the contents or which are hereby incorporated by reference.

For example, the particulate materials may include organic or inorganic pigments or lakes. Exemplary organic pigments include, for example, FD&C dyes, D&C dyes, including D&C Red, Nos. 2, 5, 6, 7, 10, 11, 12, 13, 30 and 34, D&C Yellow No. 5, Blue No. 1, Violet No. 2, and the like. Exemplary inorganic pigments include, but are not limited to, CROMOPHTHAL® Yellow, SUNFAST® Magenta, SUNFAST® Blue, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides, zinc oxides, barium oxide, composite oxides and composite hydroxides such as iron titanate, cobalt titanate and cobalt aluminate, and potassium ferricyanide ($K_3Fe(CN)_6$), potassium ferrocyanide ($K_4Fe(CN)_6$), potassium ferrocyanide trihydrate ($K_4Fe(CN)_6.3H_2O$), ferric ammonium ferrocyanide, ultramarine blue, carbon black particles, and the like.

Other suitable particulate materials include lakes, such as, for example, aluminum lakes (e.g., aluminum lakes of FD&C Yellow No. 5 and No. 6, aluminum lakes of FD&C No. 40, aluminum lakes of D&C Red Nos. 21, 22, 27, and 28, aluminum lakes of FD&C Blue No. 1, aluminum lakes of D&C Orange No. 5, and aluminum lakes of D&C Yellow No. 10), strontium lakes (e.g., strontium lakes of D&C Red No. 13), barium lakes barium lakes of D&C Red No. 12), calcium lakes (e.g., calcium lakes of D&C Red Nos. 7, 11, 31 and 34), zirconium lakes (e.g., the zirconium lake of D&C Red No. 33), Green 3 Lake, Ext. Yellow 7 Lake, Orange 4 Lake, Red 28 Lake, and the like.

The particulate material may also be based on inorganic fillers such as talc, mica, silica, and mixtures thereof or any of the clays disclosed in EP 1 640 419, the disclosure of which is hereby incorporated by reference. Other suitable particulate materials include calcium carbonate, calcium sulfate, kaolin, magnesium carbonate, carmine, barium sulfate, mica, bismuth oxychloride, zinc stearate, manganese violet, bismuth citrate, hydroxyapatite, and zirconium silicate.

In one embodiment, particulate materials may be surface modified, with, for example, fluoropolymers, to adjust one or more characteristics of the coloring agent as described in, for example, U.S. Pat. Nos. 6,471,950, 5,482,547, and 4,832,944, the contents of which are hereby incorporated by reference. Fluoropolymers may be incorporated into the present disclosure as a coating on pigment particles that at least partially covers the surface of the pigment particles. Suitable pearling pigments include without limitation bismuth oxychloride, guanine and titanium composite materials containing, as a titanium component, titanium dioxide, titanium lower oxides or titanium oxynitride, as disclosed in U.S. Pat. No. 5,340,569, the contents of which are hereby incorporated by reference.

Other suitable particulate materials include polymer blends, polymer beads, polymer fibers, plates mixed with pigments, iron oxide coated beads and fibers and the like.

Without wishing to be bound by any theory, it is believed that particulate materials having a high aspect ratio (i.e., ratio of length to width of the particle) and a small particle size provide further improved substantivity to the hair. Preferably, the particulate material is non-spherical. More preferably, the particulate material has a high aspect ratio, for example, the particulate material may have be in a plate-like shape or an elongated (e.g., cylindrical) shape. The particulate material may have an aspect ratio greater than 1:1, preferably greater than 2:1, more preferably greater than 3:1, including embodiments greater than 5:1, 8:1, 10:1, 1:15:1, 1:20, 1:25 or 1:50. The particulate material may be of any suitable size for use in a cosmetics composition. Preferably, the particulate material has a small particle size, for example, the particulate material has a median particle size from about 110 to about 2500 nm, preferably from about 50 to about 1000 nm, and more preferably from about 100 to about 500 nm, including specific embodiments where the particulate material has a median particle size of 125 nm, 150 nm, 175 nm, 200 nm, 300 nm, 400 nm, or 450 nm.

The particulate material is typically present from about 0.01% to about 25% by weight of the total composition. More typically, the particulate material will comprise from about 1% to about 15% by weight of the composition. Preferably, the particulate material will comprise from about 5% to about 10% by weight of the composition, including embodiments wherein the particulate material is present at about 6%, 7%, 8%, or 9% by weight of the composition.

In certain exemplary embodiments, the aminositicone polymer and the particulate material may be present in weight ratios from about 10:1 to about 1:10, or from about 5:1 to about 1:5, or from about 2:1 to about 1:2, or about 1:1.

The inventive cosmetic compositions will comprise a cosmetically acceptable vehicle. By "cosmetically acceptable" is meant that the vehicle is safe for contact with a human integument. It is contemplated that any cosmetically acceptable vehicle known in the art will be useful. The vehicle may comprise water or hydrophobic or hydrophilic organic solvents. Suitable hydrophilic solvents include but are not limited to, alcohols (e.g., ethanol, isopropanol, benzyl alcohol, phenylethyl alcohol, etc.), propylene glycol, butylene glycol, pentylene hexylene glycol, caprylyl glycol, glycerin, carbitol, glycol ethers such as, for example, ethylene glycol monomethyl, monoethyl and monobutyl ethers, ethers of propylene glycol such as, for example, propylene glycol monomethyl ether, dipropylene glycol and diethylene glycol alkyl ethers such as, for example, diethylene glycol monoethyl ether or monobutyl ether, and or any combinations thereof Water is a preferred vehicle component. Typically, the amount of water in the vehicle is about 20% to about 99%, more typically from about 60% to about 95% by weight.

Suitable hydrophobic vehicles include hydrocarbon oils, which may be saturated or unsaturated, have an aliphatic character and be straight or branched chained or contain alicyclic or aromatic rings. Essentially any oil is contemplated to be useful, although highly hydrophobic oils are preferred. Suitable non-limiting examples include vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like.

Suitable hydrophobic hydrocarbon oils may be saturated or unsaturated, have an aliphatic character and be straight or branched chained or contain alicyclic or aromatic rings. Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_8$-$C_{20}$ paraffinic hydrocarbons such as $C_{12}$ isoparaffin (isododecane) manufactured by the Permethyl Corporation having the trade name PERMETHYL 99A™ are also suitable. Various commercially available $C_{16}$ isoparaffins, such as isohexadecane (having the trade name PERMETHYL R™), are also suitable. Examples of preferred volatile hydrocarbons include polydecanes such as isododecane and isodecane, including for example, PERMETHYL-99A™ (Presperse Inc.) and the $C_7$-$C_3$ through $C_{12}$-$C_{15}$ isoparaffins such as the Isopar Series available from Exxon Chemicals. A representative hydrocarbon solvent is isododecane.

The vehicle may comprise a silicone oil phase which may include volatile silicone oils, non-volatile silicone oils, and combinations thereof. "Volatile silicone oil" means that the oil readily evaporates at ambient temperatures. Typically, volatile silicone oils will exhibit a vapor pressure ranging from about 1 Pa to about 2 kPa at 25° C.; will preferably have a viscosity of from about 0.1 to about 10 centistokes, preferably about 5 centistokes or less, more preferably about 2 centistokes or less, at 25° C.; and will boil at atmospheric pressure at from about 35° C. to about 250° C.

Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones polymers are available from Dow Corning under the name DOW CORNING 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al. "Volatile Silicone Fluids for Cosmetics", *Cosmetics and Toiletries*, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include DOW CORNING 200, DOW CORNING 244, DOW CORNING 245, DOW CORNING 344, AND DOW CORNING 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxarte to name a few.

Non-volatile silicone oils will typically comprise polyalkylsiloxanes, polyarylsiloxanes, polyalkylarylsiloxanes, or mixtures thereof. Polydimethylsitoxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone.

The vehicle may comprise a single phase, a dual-phase system, or an emulsion. Emulsions include oil-in-water, silicone-in-water, water-in-oil, water-in-silicone, and the like. When formulated as an emulsion, an emulsifier is typically included. Where the product is intended as a spray, it may be desirable to employ a single phase vehicle, or a dual phase vehicle comprising an aqueous phase and an oil phase, the oil phase comprising a silicone oil. Alternatively, it is contemplated that the vehicle may be substantially anhydrous or anhydrous. The substantially anhydrous or anhydrous vehicle preferably comprises a silicone oil. The term "substantially anhydrous" as used herein typically refers to a composition comprising at most 5% water, more typically to a composition comprising at most 1% water, and usually a composition comprising an amount of water absorbed from ambient conditions.

In a preferred embodiment, the vehicle is a thickened aqueous system comprising water and a thickener. The thickener may be nonionic, cationic, anionic or amphoteric. Preferably, the thickener is a cationic thickener, including, without limitation, cationic conditioning polymers. Suitable cationic polymers include, but are not limited to, cationized cellulose, cationized guar gum, diallyl quaternary ammonium salt/acrylamide copolymers, polyquaternium-37, and mixtures thereof. Among the various cationic thickeners, special mention may be made of polyquaternium-37 (INCI).

Other suitable thickeners can include, for example, acrylic acid homopolymers (sold under the trade name CARBOPOL® by Lubrizol Corp.), acrylates/$C_{10-30}$ alkyl acrylate crosspolymer (available under the trade names CARBOPOL® 1342 and 1382; and PEMULINS® TR-1 and TR-2 from BE Goodrich), acrylates/steareth-20 itaconate copolymer (available under the trade name STRUCTURE® 2001 from National Starch), acrylates/ceteth-20 itaconate copolymer (available under the trade name STRUCTURE® 3001 from National Starch), bentonite, PVM/MA decadiene crosspolymer, which is a crosspolymer of methylvinylether/maleic anhydride copolymer cross-linked with 1, 9 decadiene (commercially available under the trade name STABILEZE® QM from International Specialties Products), acrylates/steareth-20 methacrylate copolymer (sold under the trade name ACRYSOL™ ICS-1 by Rohm and Haas Co.), acrylamide/sodium acrylate copolymer (sold under the trade name HOSTACERIN® PN 73 by Hoecsht AG), acrylate copolymer (sold under the trade name ANTIL 208® by Goldschmidt), acrylic acid/acrylonitrogens copolymer (sold under the trade names HYPAN® SA-100H, SR-150H supplied by Lipo), acrylic/acrylate copolymer (sold under the trade names CARBOSET® 5 514, 515, 525, XL-19, XL-19X2, X1-28, XL-40, 526 by BF Goodrich), ammonium acrylates/acrylonitrogens copolymer (sold under the trade name HYPAN® SS-201 by Lipo), quaternium-18 bentonite, which is a sodium salt of crosslinked poly(acrylic acid) (sold under the trade names PNC 430, PNC 410, PNC 400 by 3V), stearalkonium bentonite (sold under the trade name CLAYTON® by Southern Clay Products), quaternium-18 hectorite (BENTONE® 38), stearalkonium hectorite (BENTONE® 27), poly(acrylic acid) (sold under the trade names CARBOPOL® 400 by BF and AQUATREAT® by Alco), trihydroxystearin (commercially available under the trade names THIXICIN® by Rheox and FLOWTONE™ by Southern Clay Products), dimethylaminoethyl methacrylamide and acrylamide copolymer (SALCARE® SC63 from Ciba Specialties), acrylic polymer anionic or cationic thickening agents (sold under the trade name SYNTHALEN™ by 3V), polyacrylate-1 crosspolymer (INCI) (sold under the trade name CARBOPOL® Aqua CC by Lubrizol Corp.), sodium acrylate copolymer (sold under the trade name TINOVIS® ADM by Ciba), and polyacrylamidomethylpropane sulfonic acid (sold under the trade name COSMEDIA HSP-1180 by Cognis Care Chemicals).

The thickener preferably comprises from about 0.001 to about 25%, more preferably at about 0.1% to about 15%, and more preferred still from about 0.5% to about 5% by weight of the vehicle.

The compositions of the invention may optionally comprise other active and inactive ingredients typically associated with hair care products. The nature of these other ingredients and their amounts should preferably be suitable for formulating a hair care product. Preferably, these other ingredients include at least one bioactive ingredient for improving the keratin fiber. It is within the skill in the art to choose additional active and/or inactive ingredients for a hair care product. Suitable other ingredients include, but are not limited to, amino acids, antioxidants, chelating agents, colorants, emollients, emulsifiers, excipients, fillers, fragrances, gelling agents, humectants, minerals, moisturizers, photostabilizing agents (e.g., UV absorbers), preservatives, stabilizers, staining agents, surfactants, viscosity and/or rheology modifiers, vitamins, waxes, and mixtures thereof. The inventive hair care product of the present invention can also include antidandruff, deodorant, sunscreen and/or antiperspirant ingredients.

The compositions may be in any suitable form, including but not limited to, gels, creams, liquids, emulsions, sprays, lotions, and the like. The vehicle may comprise a single phase, a dual-phase system, or an emulsion. Emulsions include oil-in-water, silicone-in-water, water-in-oil, water-in-silicone, and the like. When formulated as an emulsion, an emulsifier is typically included. The composition of the present invention may be any suitable hair care or cosmetic composition, including mascara, hair colorant, shampoo, conditioner, and styling products gel, mousse, etc.), amongst others.

The composition may be used as a coloring treatment or as a highlighting treatment and is non-damaging and less irritating than typical hair coloring products that use chemical dyes that penetrate the hair or that react inside the hair shaft. The treatment can be a one-time treatment, or may be used on a regular basis for a continuous color treatment. The compositions of the present invention may be used to deliver rich semi-permanent color to substrates including hair, eyes, skin, lips, and nails. The compositions may also be used to impart color to any particular location, such as roots of keratin fibers, eyelashes, eyebrows, beards, and the like. In particular, the compositions may be used to provide long-lasting root touch-up for artificially colored hair or to cover gray hair. Alternatively, the composition may be used to deposit gradual color to the hair with each application.

The inventive composition may be applied onto dry hair or wet hair (hair of the body, scalp, beard, mustache, eyelashes, eyebrows, etc.) to impart a long-wearing and transfer-resistant artificial color. Thus, for example, the composition may be applied to the hair while it is dry, when it is only minimally wet, or after submersion in water. Typically, the composition may be applied to hair before shampooing of the hair. Alternatively, the composition may be applied to the hair following shampooing of the hair. The composition may also be applied during shampooing of the hair. In addition, the hair care composition can be re-applied at any time, as the consumer desires. For example, the hair care composition may be re-applied twice a day, daily, every two days, weekly, or biweekly. In one embodiment, the hair care composition may be re-applied to the hair before every wash. The compositions are beneficially applied after each shampooing, but resist one, two, three, four, six, eight, ten or even more shampooings before reapplication is required.

The compositions of the present invention may be formulated to impart long-wearing color to any keratinous surface, including skin, lips, nails, etc. in particular, it is contemplated that the compositions of the present invention may be formulated with sunscreen particulate materials to provide a durable sunscreen formulation for application to the skin. The cosmetic compositions of the present invention may be applied to the skin, lip or nails, and may be re-applied at any time.

EXAMPLE I

A hair care composition according to the invention with an aminosilicone polymer having at least one diamino functional group and a functional group equivalent weight (FGEW) from about 1,000 to about 2,000 g/mol, was investigated to determine the wash-resistance of color imparted on hair treated with the hair care composition. Compositions were prepared according to Table 1.

TABLE 1

| Components | Sample Number: | | | | | |
|---|---|---|---|---|---|---|
| | 1 | 2 | 3 | 4 | 5 | 6 |
| | Weight % | | | | | |
| Amodimethicone (GE SME 253) | 5 | — | — | — | — | — |
| Aminosilicone (SF-1708) | — | 5 | — | — | — | — |
| Aminosilicone (Shin-Etsu KF-8002) | — | — | 5 | — | — | — |
| Aminosilicone (Shin-Etsu KF-8005) | — | — | — | 5 | — | — |
| Aminosilicone (Blustar ADM-211) | — | — | — | — | 5 | — |
| Aminosilicone (Wacker HC303) | — | — | — | — | — | 5 |
| Red Iron Oxide (C33-128) from Sun Chemical in a 50/50 blend of ethanol | 2 | 2 | 2 | 2 | 2 | 2 |

TABLE 1-continued

| Components | Sample Number: | | | | | |
|---|---|---|---|---|---|---|
| | 1 | 2 | 3 | 4 | 5 | 6 |
| | | | Weight % | | | |
| 50/50 blend of Ethanol and XIAMETER PMX-0345 cyclosiloxane blend from Dow Corning Corp. (65% cyclopentasiloxane/ 35% cyclohexasiloxane) | q.s. | q.s. | q.s. | q.s. | q.s. | — |
| 50/50 propylene glycol/ water mixture | — | — | — | — | — | q.s. |
| Total: | 100 | 100 | 100 | 100 | 100 | 100 |

Sample 1 includes Amodimethicone (and) C11-15 Pareth-7 (and) Laureth-9 (and) Glycerin (and) Trideceth-12 (INCI name), available from GE Bayer Silicone under the trade name GE SME™ 253. The GE SME 253 material has a viscosity of about 2,000 mm$^2$/s at 25° C. Sample 2 includes a branched aminosilicone polymer having a modification of an aminoethylaminopropyl functional group available from Momentive Specialty Chemicals Inc. under the trade name SF1708. The SF1708 material is an aminoethylaminopropylpolysiloxane (CAS Reg. No. 71750-79-3), which has a FGEW of 1,250 g/mol and a viscosity of 1250-2500 mm$^2$/s at 25° C. Sample 3 includes an aminosilicone polymer having a modification of an aminoethylaminopropyl functional group available from Shin-Etsu Chemical Co., Ltd. under the trade name KF-8002. The KF-8002 material has a FGEW of 1,700 g/mol and a viscosity of 1,100 mm$^2$/s at 25° C. Sample 4 includes an aminosilicone polymer having a modification of an aminoethylaminopropyl functional group available from Shin-Etsu Chemical Co., Ltd. under the trade name KF-8005. The KF-8005 material has a FGEW of 11,000 g/mol and a viscosity of 1,200 mm$^2$/s at 25° C. Sample 5 includes an aminosilicone polymer having a modification of a &amino functional group and methoxy terminal ends available from Bluestar Silicones USA Corp. under the trade name ADM-211. The ADM-211 material has a FGEW of 6,500 g/mol and a viscosity of 1,200 mm$^2$/s at 25° C. Sample 6 includes an aminosilicone available from Wacker Chemie AG under the trade name HC303.

Hair samples of fine density platinum bleached hair were obtained from International Hair Importers. Hair tresses were cut to a dimension of ½ inch width and 6 inches in length (including a silicone tab attached to the hair tress). Using a 1 mL syringe, 0.75 mL of a hair care composition was applied to the hair sample and manually distributed throughout by repeat downward motions for 30 seconds. Samples sat undisturbed for at least 12 hrs before washing.

The amount of color deposited onto the hair sample by application of the hair care composition was measured using the Hunter L, a, b Color Scale with a Minolta colorimeter at 5 different locations on each hair sample. The Hunter L, a, b Color Scale involves three different variables: the variable "L", which runs from 0 to 100 and represents the Lightness axis, where a value of 100 would represent white and a value of 0 would represent black; the variable "a" has no numerical limits, and represents the red-green axis, where a positive value would represent red and a negative value would represent green; and the variable "h" has no numerical limits, and represents the blue-yellow axis, where a positive value would represent blue and a negative value would represent yellow. A total color difference represented by ΔE may be calculated to demonstrate the total color difference, or the overall change in hair tress color, as compared to untreated hair, according to the following formula:

$$\Delta E = \sqrt{[(L_{treated} - L_{untreated})^2 + (a_{treated} - a_{untreated})^2 + (b_{treated} - b_{untreated})^2]}$$

After the color measurement, the hair sample was washed, rinsed, dried and measured for color retention a total of five (5) times. Each time, the hair sample was first rinsed under running warm water at a temperature between 95 to 105° F., for 30 seconds. Excess water from the hair samples were manually removed by squeezing the hair samples between the middle and index fingers three (3) times. To wash each hair sample, 0.5 mL of a commercial shampoo (ADVANCED TECHNIQUES Color Reviving Shampoo from Avon Products, Inc.) was measured and applied to the hair using a syringe. The shampoo was manually distributed throughout the hair sample by applying repeat downward motions for 30 seconds. The shampooed hair sample was placed under running warm water, at a temperature between 95 to 105° F., and rinsed for 30 seconds, or until all suds were removed. Excess water from the hair sample was manually removed by squeezing the hair sample between the middle and index fingers. Conditioner may be optionally applied. The hair sample was then hung using a hair tress holder, detangled using a large toothed comb, and left to air dry until all of the residual moisture in the hair sample had been evaporated. The color retention of each hair sample was measured after each wash using the Hunter L, a, b Color Scale with a Minolta colorimeter at five different locations on each hair sample, and the ΔE value for each measurement was determined based on these measurements.

The results of the color retention test for each of Samples 1 through 6 are shown in FIG. 1. As can be seen from FIG. 1, a significant amount of red iron oxide color was deposited on the hair samples for all six (6) samples. However, only Samples 2 and 3 maintained about the initial level of color after five (5) shampoo washes. Although Samples 1 and 6 provided some color retention, the amount of color declined after five (5) washes. Samples 4 and 5 demonstrated drastic reduction in color following five (5) washes.

EXAMPLE II

Hair care compositions according to the invention with various aminosilicones were investigated regarding the wash-resistance of color imparted on hair treated with the hair care composition. Samples 7-17 were prepared by combining 2.5% by weight of an aminositicone polymer listed below in Table 2, 2% by weight of black iron oxide (C33-134) from Sun Chemical in a 5% Xiameter PMX-0345 cyclosiloxane blend from Dow Corning Corp. (65% cyclopentasiloxane/ 35% cyclohexasiloxane), 25% ethanol, 10% propylene glycol, 5% PEG-10 dimethicone (Gransurf 77 from Grant Industries), and 51% deionized water.

TABLE 2

| Sample No. | Aminosilicone | Modification Type | Viscosity (mm$^2$/s) | FGEW (g/mol) |
|---|---|---|---|---|
| 7 | Shin-Etsu KF-865 | Mono Amino (aminopropyl) | 110 | 5,000 |

TABLE 2-continued

| Sample No. | Aminosilicone | Modification Type | Viscosity (mm²/s) | FGEW (g/mol) |
|---|---|---|---|---|
| 8 | Shin-Etsu KF-868 | | 90 | 8,800 |
| 9 | Shin-Etsu KF-393 | Diamino | 70 | 350 |
| 10 | Shin-Etsu KF-880 | (aminoethyl- | 650 | 1,800 |
| 11 | Shin-Etsu KF-8004 | aminopropyl) | 800 | 1,500 |
| 12 | Shin-Etsu KF-8002 | | 1,100 | 1,700 |
| 13 | Shin-Etsu KF-8005 | | 1,200 | 11,000 |
| 14 | Shin-Etsu KF-861 | | 3,500 | 1,600 |
| 15 | Shin-Etsu X-22-3939A | Amino Polyether | 3,300 | 1,700 |
| 16 | Bluestar ADM-211 | Methoxy Capped + Diamino | 1,100 | 6,500 |
| 17 | Momentive SF-1708 | Branched Amino Fluid (aminoethyl-aminopropyl) | 1250-2500 | 1,250 |

Each of Samples 7 through 17 was tested in the same manner as described for Example I. The results of the color retention test for each of Samples 7 through 17 are shown below in Table 3. For example, where the hair care composition provided measurable pigment color deposition onto the hair sample, an entry of "yes" is indicated in the column labeled "Pigment Color Deposition" in Table 3. After the first wash, third wash and fifth wash, if the amount of color remaining was greater than 80% of the initial pigment color deposited (i.e., where ΔE after the wash was greater than or equal to 80% of the ΔE of the initial sample post-treatment), then an entry of "yes" was entered in the column in Table 3 reflecting the number of washes.

TABLE 3

| | Pigment Color | Color Retention (80% of Initial) | | |
|---|---|---|---|---|
| Sample No. | Deposition | 1X Wash | 3X Wash | 5X Wash |
| 7 | yes | no | no | no |
| 8 | yes | no | no | no |
| 9 | yes | yes | no | no |
| 10 | yes | yes | yes | yes |
| 11 | yes | yes | yes | no |
| 12 | yes | yes | yes | yes |
| 13 | yes | no | no | no |
| 14 | yes | yes | yes | yes |
| 15 | yes | no | no | no |
| 16 | yes | yes | no | no |
| 17 | yes | yes | yes | yes |

As can be seen from Table 3, compositions comprising mono-amino silicones (Samples 7 and 8) or amino-polyether modified silicones (Sample 15) in combination with a pigment did not impart long-wearing color that could be sustained after a single shampoo wash. In contrast, a branched aminosilicone polymer having an aminoethylaminopropyl functional group, e.g., the SF1708 material (Sample 17) or a linear aminosilicone polymer having an aminoethylaminopropyl functional group (Samples 10, 11, 12 and 14) and a FGEW from 1,500 to 1,800 g/mol retained significant color after 5 shampoos.

In addition, the durability of black iron oxide (C33-134 from Sun Chemical in a 50/50 blend of ethanol) and amodimethicone coated black iron oxide (BBO-NS2 from Kobo) were investigated in relation to the wash-resistance of color imparted on hair treated with either pigment. Neither black iron oxide nor the amodimethicone coated black iron oxide provided a color deposition where the ΔE is greater than 35.

EXAMPLE III

An exemplary hair care composition is provided in Table 4.

TABLE 4

| Component | Weight % |
|---|---|
| Amodimethicone | 2.5 |
| Cyclopentasiloxane | 4 |
| 50 cPs Dimethicone | 1 |
| Black Iron Oxide | 2.5 |
| Lauryl PEG-9 PDMS Dimethicone | 1 |
| Dimethicone PEG-10/15 crosspolymer/dimethicone blend | 4 |
| VELVESIL DM ™ | 1 |
| 65% Polyquaternium-37 | 0.25 |
| Sodium Chloride | 1 |
| Capgly/phenoxyethanol | 1 |
| Glycerin | 2 |
| Water | q.s. |
| Total: | 100 |

Figure 2:
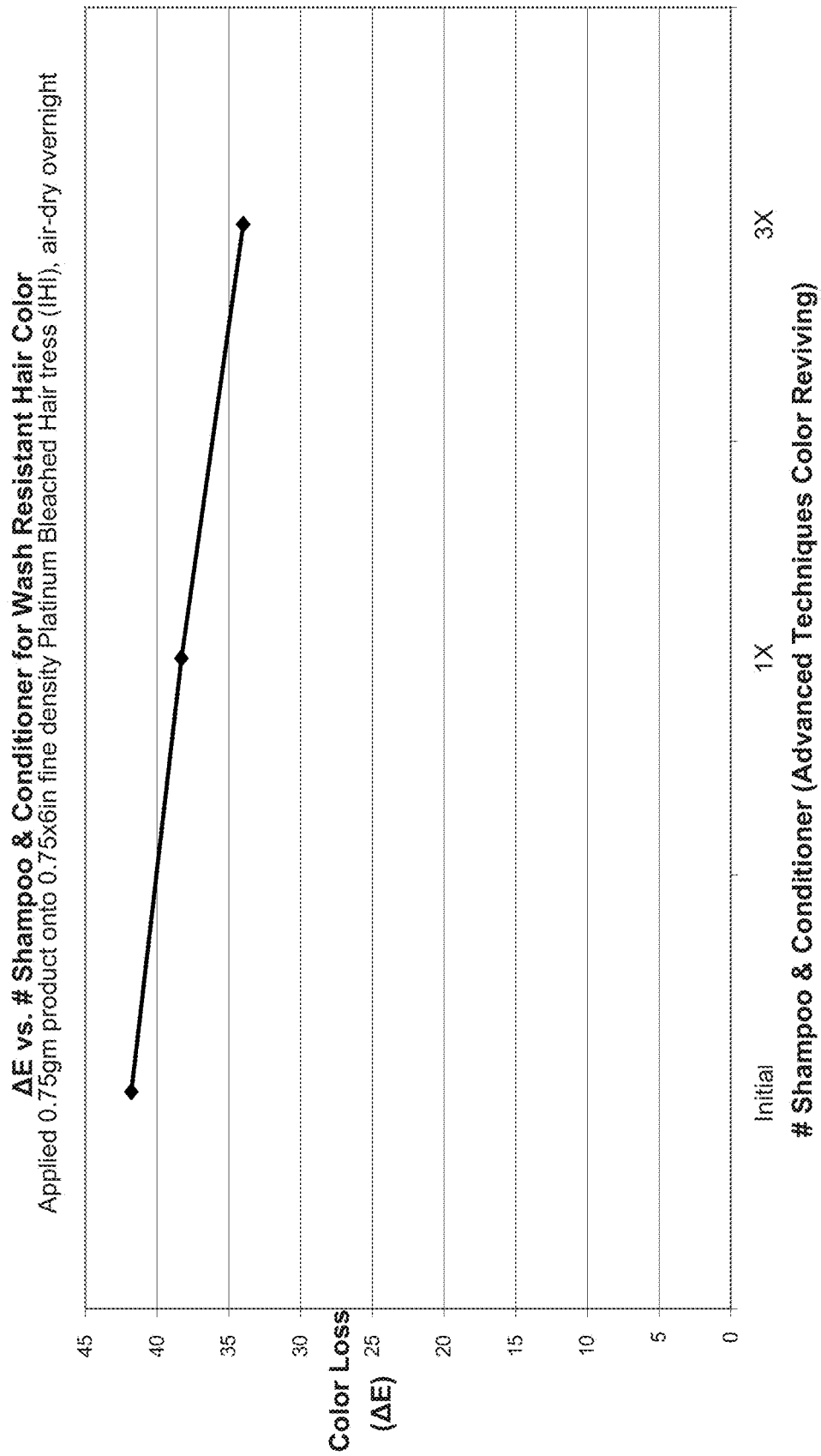
FIG. 2 shows a color retention test for the hair care composition of Table 4.

VELVESIL DM SILICON™ has the INCI name Dimethicone (and) Cetearyl Dimethicone Crosspolymer, and is available commercially. The hair care composition of Table 4 was tested by applying 0.75 g of the composition to fine density platinum bleached hair tresses obtained from International Hair Importers (cut to a dimension of ¾ inch width and 6 inches in length). The hair tresses were washed, rinsed, dried, and measured three (3) times, in the same manner as described in Example I. The results of this color retention test are shown in FIG. 2.

Figure 3:
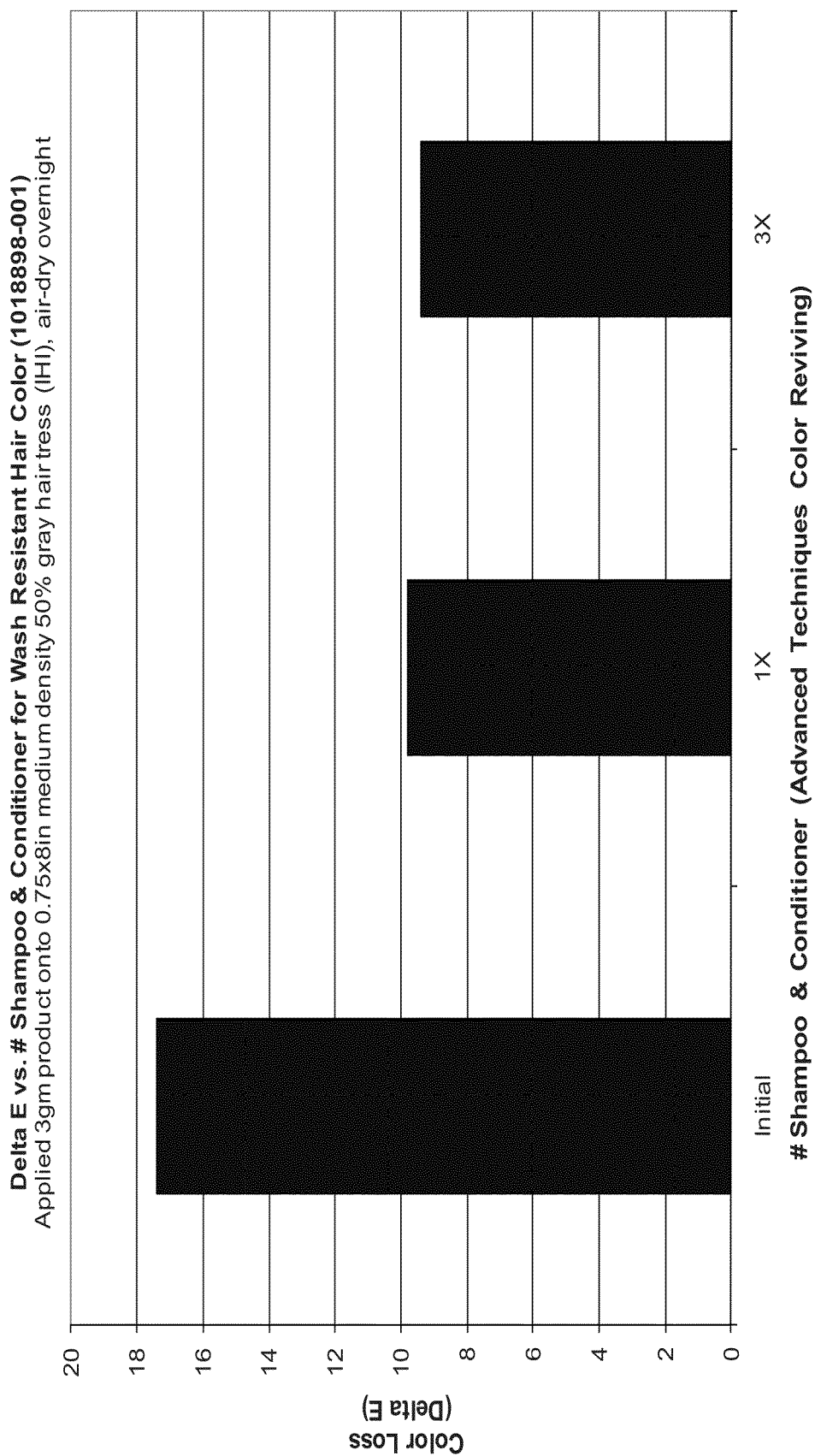
FIG. 3 shows a color retention test for the hair care composition of Table 4 tested on gray hair tresses after being washed, rinsed and dried.

The hair care composition of Table 4 was also tested by applying 3 mg of the composition to medium density gray hair tresses obtained from International Hair Importers (cut to a dimension of ¾ inch width and 8 inches in length). The hair tresses were washed, rinsed, dried and measured three (3) times, in the same manner as described in Example I. The results of this color retention test are shown in FIG. 3.

EXAMPLE IV

A mascara formulation having an aminosilicone polymer having at least one diamino functional group and a functional group equivalent weight from about 1,000 to about 2,000 g/mol, was investigated in relation to the wash-resistance of color imparted by the mascara formulation. Exemplary comparative compositions were prepared according to Table 5.

TABLE 5

| | Sample No.: | |
|---|---|---|
| | M1 | M2 |
| Component | Weight % | |
| SF-1708 Aminosilicone | 0 | 2.5 |
| Cyclopentasiloxane | 6.5 | 4 |
| 50 cPs Dimethicone | 1 | 1 |
| POP (2M) myristyl ether propionate | 3 | 3 |
| Black Iron Oxide | 5 | 5 |
| D&C Black #2 | 0.5 | 0.5 |
| Lauryl PEG-9 PDMS Dimethicone | 1 | 1 |
| Dimethicone PEG-10/15 crosspolymer/dimethicone blend | 4 | 4 |
| Velvesil DM | 1 | 1 |
| Polyquaternium 7 | 0.5 | 0.5 |
| Capgly/phenoxyethanol | 1 | 1 |

TABLE 5-continued

| | Sample No.: | |
|---|---|---|
| Component | M1 | M2 |
| | Weight % | |
| Glycerin | 2 | 2 |
| Water | q.s. | q.s. |
| Total: | 100 | 100 |

Figure 4:
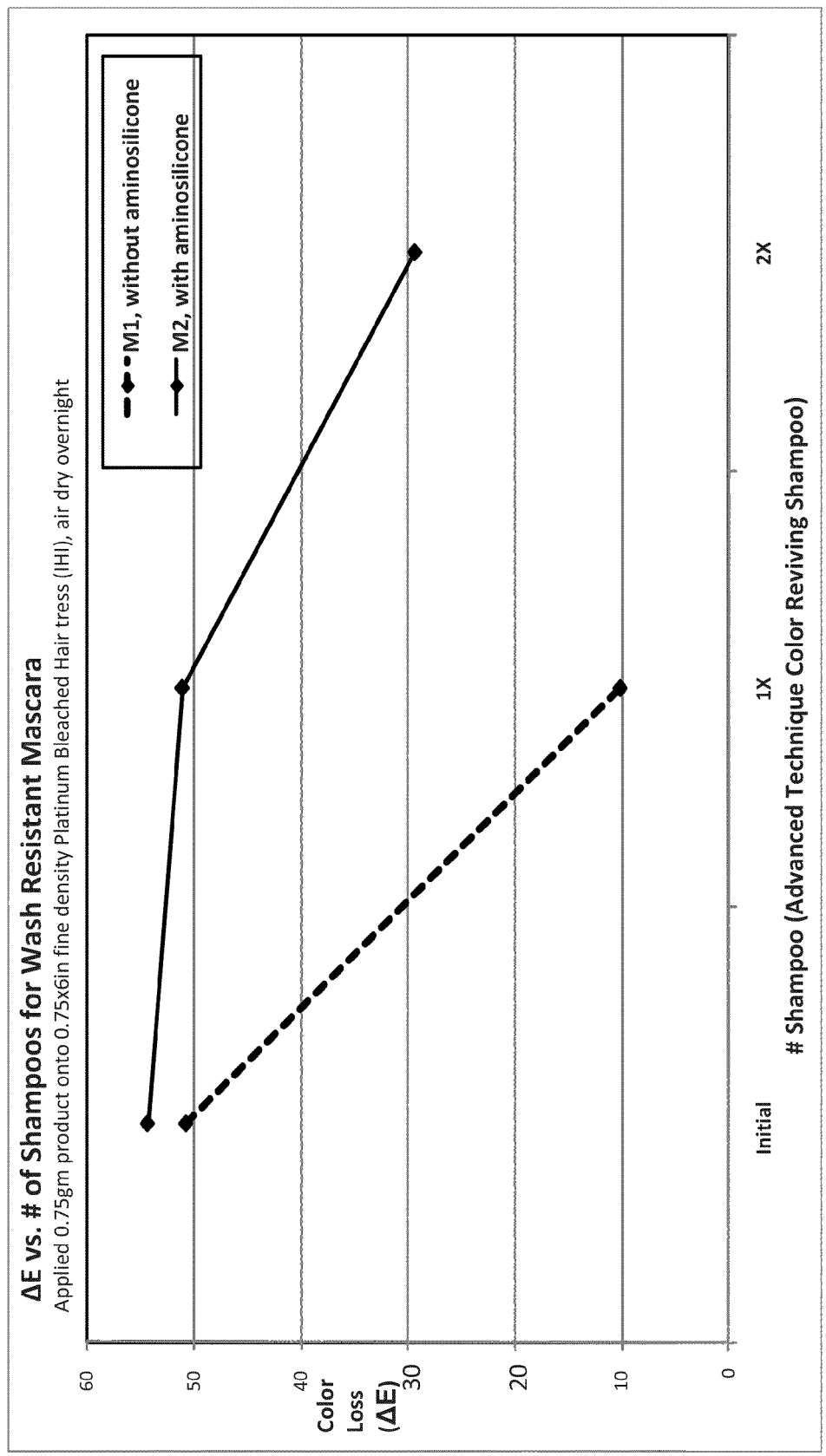
FIG. 4 shows the results of a color retention test for Samples M1 and M2 in a mascara test.

Both Sample M1 and Sample M2 were tested in the same manner as in Example I, with the results of the color retention test for Samples M1 and M2 illustrated in FIG. 4. As shown in FIG. 4, the mascara composition containing the SF-1708 aminosilicone polymer (Sample M2), which is a branched aminosilicone polymer having an aminoethylaminopropyl functional group and a functional group equivalent weight of 1,250 g/mol, retains color after one wash as compared to an otherwise identical mascara formulation without the aminosilicone polymer (Sample M1). Moreover, the mascara formulation containing the aminosilicone polymer (Sample M2) retained more color even after two (2) washes as compared to the mascara formulation of Sample M1.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended All publications cited herein are incorporated by reference in their entirety.

The invention claimed is:

1. A method for imparting a long-wearing color to hair of the scalp, comprising applying to said hair of the scalp a composition comprising:
   (a) at least one aminosilicone polymer having at least one aminoethylaminopropyl group and a functional group equivalent weight (FGEW) from 1,000 to 2,000 g/mol, and
   (b) a non-spherical particulate material, wherein said non-spherical particulate material is a pigment or lake,
   wherein said aminosilicone polymer improves retention of said particulate material on the keratinous substrate over time as compared to an otherwise identical composition in the absence of said aminosilicone, and
   wherein said composition is applied to the hair of the scalp prior to shampooing, and wherein the retained particulate material in said composition imparts a long wearing color to the hair of the scalp.

2. The method according to claim 1, wherein said aminosilicone polymer has a viscosity from about 500 to about 5,000 cP at 25° C.

3. The method according to claim 1, wherein said aminosilicone polymer is branched.

4. The method according to claim 1, wherein said aminosilicone polymer has the structure:

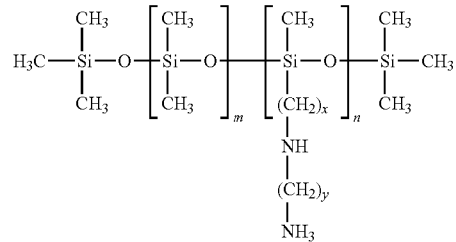

where
   x is 3,
   y is 2, and
   m and n are independently each an integer from 1 to 5,000 and are selected to provide a FGEW from 1,000 to 2,000 g/mol.

5. The method according to claim 1, wherein said pigment is an iron oxide pigment.

6. The method according to claim 1, wherein said non-spherical particulate material has a plate-like or elongated shape.

* * * * *